US011344881B2

(12) United States Patent
Emerson et al.

(10) Patent No.: US 11,344,881 B2
(45) Date of Patent: *May 31, 2022

(54) SEPARATORS FOR BLOOD COLLECTION TUBES

(71) Applicants: The Regents of the University of California, Oakland, CA (US); University of Maryland, College Park, MD (US)

(72) Inventors: Jane F. Emerson, Irvine, CA (US); Mohamad Al-Sheikhly, Potomac, MD (US)

(73) Assignees: The Regents of the University of California, Oakland, CA (US); University of Maryland, College Park, College Park, MD (US)

( * ) Notice: Subject to any disclaimer, the term of this patent is extended or adjusted under 35 U.S.C. 154(b) by 339 days.

This patent is subject to a terminal disclaimer.

(21) Appl. No.: 15/522,770

(22) PCT Filed: Oct. 26, 2015

(86) PCT No.: PCT/US2015/057359
§ 371 (c)(1),
(2) Date: Apr. 27, 2017

(87) PCT Pub. No.: WO2016/069469
PCT Pub. Date: May 6, 2016

(65) Prior Publication Data
US 2018/0154354 A1 Jun. 7, 2018

(30) Foreign Application Priority Data
Oct. 28, 2014 (EP) .................................. 14190681

(51) Int. Cl.
*B01L 3/00* (2006.01)
*G01N 33/49* (2006.01)
*B01D 21/26* (2006.01)

(52) U.S. Cl.
CPC ........ *B01L 3/50215* (2013.01); *G01N 33/491* (2013.01); *B01D 21/262* (2013.01);
(Continued)

(58) Field of Classification Search
CPC ............ B01L 3/50215; B01L 2200/06; B01L 2200/12; B01L 2300/12; B01L 2400/0677; G01N 33/491
See application file for complete search history.

(56) References Cited

U.S. PATENT DOCUMENTS

| 4,848,418 A | 4/1989 | Saunders |
| 4,867,887 A | 9/1989 | Smith |
(Continued)

FOREIGN PATENT DOCUMENTS

| CN | 101909760 | 12/2010 |
| CN | 102227497 | 10/2011 |
(Continued)

OTHER PUBLICATIONS

International Search Report and the Written Opinion for PCT/US15/57359 International filing date Oct. 26, 2015; ISR dated May 6, 2016.

(Continued)

*Primary Examiner* — Benjamin R Whatley
(74) *Attorney, Agent, or Firm* — Joseph A. Andelin; Fish IP Law, LLP

(57) ABSTRACT

Sample collection tubes and methods of producing the same are provided. Contemplated collection tubes comprise a tube having a separator substance disposed therein. In some aspects, the separator substance preferably maintains a predetermined flowability during irradiation or heat sterilization, and can subsequently polymerize upon exposure to a UV light or other suitable source.

19 Claims, 1 Drawing Sheet

(52) U.S. Cl.
CPC ....... *B01D 2221/10* (2013.01); *B01L 2200/06* (2013.01); *B01L 2200/12* (2013.01); *B01L 2300/12* (2013.01); *B01L 2400/0677* (2013.01)

(56) References Cited

U.S. PATENT DOCUMENTS

| | | | |
|---|---|---|---|
| 5,461,124 | A | 10/1995 | Ritter et al. |
| 5,695,689 | A | 12/1997 | Gupta et al. |
| 5,859,280 | A | 1/1999 | Arhancet |
| 6,497,325 | B1 | 12/2002 | Dicesare et al. |
| 7,673,758 | B2 | 3/2010 | Emerson |
| 7,674,388 | B2 | 3/2010 | Emerson |
| 7,775,962 | B2 | 8/2010 | Emerson |
| 7,780,861 | B2 | 8/2010 | Emerson |
| 7,971,730 | B2 | 7/2011 | Emerson |
| 8,206,638 | B2 | 6/2012 | Emerson |
| 8,282,540 | B2 | 10/2012 | Emerson |
| 8,642,343 | B2 | 2/2014 | Inoue et al. |
| 9,339,845 | B2 | 5/2016 | Minagawa |
| 2002/0147094 | A1 | 10/2002 | Dolecek |
| 2005/0056954 | A1 | 3/2005 | Devlin et al. |
| 2007/0187341 | A1 | 8/2007 | Emerson |
| 2008/0132874 | A1 | 6/2008 | Emerson |
| 2009/0129973 | A1 | 5/2009 | Emerson |
| 2009/0139937 | A1* | 6/2009 | Emerson ............ B01L 3/50215 210/782 |
| 2011/0250105 | A1 | 10/2011 | Suto et al. |
| 2012/0308446 | A1 | 12/2012 | Inoue et al. |
| 2013/0310772 | A1* | 11/2013 | Minagawa ............ C08C 19/28 604/265 |
| 2014/0073990 | A1 | 3/2014 | Holmes et al. |
| 2014/0113795 | A1 | 4/2014 | Emerson et al. |

FOREIGN PATENT DOCUMENTS

| | | |
|---|---|---|
| CN | 102428125 | 4/2012 |
| CN | 103421205 | 12/2013 |
| CN | 103421205 B | 7/2019 |
| EP | 2360470 A1 | 8/2011 |
| EP | 2664627 A1 | 11/2013 |
| EP | 3015168 A1 | 5/2016 |
| EP | 3015169 A1 | 5/2016 |
| JP | H063356 A | 1/1994 |
| JP | 2001122909 A | 5/2001 |
| WO | 2013011947 A1 | 1/2013 |
| WO | 2014066049 A1 | 5/2014 |
| WO | 2016/069469 A2 | 5/2016 |
| WO | 2016069468 A1 | 5/2016 |

OTHER PUBLICATIONS

Sun, K. et al. "A new method for centrifugal separation of blood components: Creating a rigid barrier between density-stratified layers using a UV-curable thixotropic gel" Cite this: J. Mater. Chem., 2012, 22, 2378 DOI: 10.1039/c2jm14818h.

ISA/US, International Search Report and Written Opinion, Int'l Appln. No. PCT/US2015/057359, dated May 6, 2016 (10 pages).
Laura Nystrom; A comparison of the antioxidant properties of steryl ferulates with tocopherol at high temperatures; Science Direct; Food Chemistry 101 (2007) 947-954.
Tony Wang; Antioxidant Activity of Phytosterols, Oryzanol, and Other Phytosterol Conjugates; Department of Food Science and Human Nutrition; JAOCS, vol. 79, No. 12 (2002).
English Translation of Japanese Application No. JP2017523528 dated Jul. 30, 2019, 2 pages.
English Translation of Japanese Application No. JP2017523530 dated Jul. 30, 2019, 2 pages.
Examination Report for Australian Patent Application No. 2015339569 dated Apr. 6, 2020, 2 pages.
Examination Report for Australian Patent Application No. 2015339570 dated Sep. 4, 2020, 8 pages.
Extended European Search Report for Application No. EP14190680 dated Jun. 1, 2015, 4 pages.
International Search Report and Written Opinion for Application No. PCT/US15/57357, dated Jan. 19, 2016, 11 pages.
Office action for Brazil Application No. BR112017009063-5 dated Dec. 10, 2019, 4 pages.
Office action for Brazil Application No. BR112017009065-1 dated Jan. 28, 2020, 6 pages.
Office action for Canadian Application No. 2966331 dated Jun. 12, 2018, 3 pages.
Office action for Canadian Application No. 2966335 dated Jan. 7, 2019, 3 pages.
Office action for Canadian Application No. 2966335 dated Sep. 12, 2019, 3 pages.
Office action for Canadian Application No. 2966335 dated May 28, 2018, 4 pages.
Office action for Chinese Application No. 2015800689017 dated Jan. 3, 2019, 4 pages.
Office action for Chinese Application No. 201580068901.7 dated Mar. 3, 2020, 4 pages.
Office action for Chinese Application No. 201580068901.7 dated Aug. 21, 2019, 8 pages.
Response to OA dated Jul. 7, 2019 for Canadian Application No. 2966335 dated Jan. 7, 2019, 6 pages.
Response to OA dated Jun. 5, 2018 for Canadian Application No. 2966331 dated Jun. 12, 2018, 6 pages.
Response to OA dated Oct. 2, 2018 for Canadian Application No. 2966335 dated May 28, 2018, 9 pages.
Office Action for Australian Application No. 2015339570; dated Nov. 23, 2020.
Office Action for Chinese Application No. 2015800689110; dated Jan. 25, 2019.
Extended European Search Report for European Application No. 14190681.8; dated Apr. 28, 2015.
Office Action for Japanese Application No. 2017-523530; dated Jul. 30, 2019.
Office Action—Communication Pursuant to Article 94(3) EPC for European Patent Application 14190681.8; dated Apr. 28, 2015.

* cited by examiner

SEPARATORS FOR BLOOD COLLECTION TUBES

This application claims priority to European Patent Application serial number 14190681.8, filed Oct. 28, 2014. This and all other extrinsic references are incorporated herein by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is sample separation technologies.

BACKGROUND

Analysis of blood samples often requires separation of whole blood into two or more fractions, for example, a serum fraction and a cell-containing fraction. It is well known in the art that whole blood separation can be carried out through centrifugation by disposing whole blood into a blood collection tube, placing the tube into a centrifuge, and spinning down the blood.

Unfortunately, once the blood separates, the fractions of the whole blood can remix causing contamination of the fractions through diffusion, agitation, sample extraction, or other undesirable interaction. Ideally, the two fractions should remain isolated to ensure no contamination occurs when accessing the desired fraction.

In an attempt to overcome the problems discussed above, efforts have been put forth in providing separator gels disposed in a bottom portion of a tube. These separator gels are intended to help preserve analyte stability, to decrease manual labor (pipetting to a secondary tube), and allow for delayed processing that may result from the need to transport specimens from draw locations to testing facilities. Some functional and performance properties of the gels typically include the following: (1) the gel properties prevent flow before use to eliminate reflux potential during blood draw; (2) the gel has a density value between cells and serum/plasma (about 1.04 specific gravity); (3) the gel is thixotropic (shear thins in centrifuge under ordinary clinical lab protocols); (4) the gel liquefies and flows past blood cells and proteins during centrifugation; and (5) the liquefied gel re-gels at a layer between cells and serum after centrifugation and adheres to the tube wall. Furthermore, the components of the gel generally should not interfere with blood components or assays used in the clinical lab.

Unfortunately, known separator gels suffer from one or more direct and indirect disadvantages, including for example: interference (certain assays are known to be problematic); analyte drift due to permeability, cell trapping in or on the surface of the gel; physical contamination of analyzer probes or with electrophoresis gels; inaccuracies caused by re-spinning; the need for aliquoting (with attendant manual labor costs and the potential for relabeling errors); incomplete aspiration which negatively affects standardization and results in wastage; and storage/shipping issues such as gel dislodging, freeze-thaw issues, and the inability to remix a sample with a soft gel barrier.

In an attempt to overcome some of the problems associated with separator gels, effort has been put forth in attempting to provide compositions and methods for whole blood separation that ensures the separated factions of whole blood are effectively protected against contamination due to undesirable sample interactions. For example, Applicant has obtained several patents for previous efforts directed towards photopolymer serum separators and methods (e.g., U.S. Pat. Nos. 7,674,388, 7,673,758, 7,775,962, 7,971,730, 7,780,861, 8,206,638, 8,282,540).

Photopolymer serum separators can be advantageous in providing a solid interface (when the photopolymer gel is polymerized) between cells and serum or plasma, which allows for complete aspiration of the sample. Additionally, a tube comprising some photopolymer separator gels (before polymerization to form a solid) can be shipped, refrigerated or frozen with repeated freeze-thaw cycles. Still further, the tube can be mixed without disrupting the barrier to ensure uniform sampling of the test fraction (e.g., blood is not remixed when tubes are agitated), the tube is free of soft gel material (after polymerization) that can clog analyzer probes or pipette tips, or come into contact with test fraction to interfere with susceptible laboratory assay methods (e.g., electrophoresis).

Unfortunately, some known separator compositions and methods have been problematic for various reasons, including the high cost of photocurable compositions, the need to formulate a thixotropic composition, the heat produced in exothermic polymerization reactions which may affect analytes, inability to sterilize via irradiation while maintaining flowability of the separator compositions for subsequent UV curing (e.g., after shipment of the sterilized composition in sample collection tubes), and volume-dependent UV-light exposure requirements.

Thus, there is still a need for improved separation technologies.

SUMMARY

The present inventive subject matter provides apparatus, compositions, systems and methods that generally attempt to solve the problems described above by providing a sample collection tube comprising: (i) a tube having a lumen, and (ii) a composite separator substance disposed within the lumen, wherein the separator substance comprises a gel component layer material and a photocurable sealant component layer material. More specifically, the gel component layer material could comprise a thixotropic separator gel that is formulated to become a liquid when stirred or shaken, and the photocurable sealant component layer material could comprise a photopolymer sealant. The gel component layer material and the photocurable sealant component layer material could be separate layers (e.g., before irradiation sterilization, before centrifugation, before curing, after irradiation sterilization, after centrifugation, after curing, before and after irradiation sterilization, before and after centrifugation, before and after curing). Additionally or alternatively, the gel component layer material and the photocurable sealant component layer material could comprise a mixture.

The photocurable sealant component could optionally be anti-thixotropic. Additionally or alternatively, the photocurable sealant component could be formulated to polymerize within ten minutes to a hardness of at least 1 on the Shore 00 hardness scale when triggered by a suitable energy source (e.g., UV light (arc lamps, microwave power bulbs, LEDs)).

There are numerous factors that can affect the curing of the photocurable sealants and photocurable separator substances of the inventive subject matter. The suitable light source could emit a light having an intensity of between 5-100 W/cm$^2$, between 10-75 W/cm$^2$, between 15-50

W/cm², or any other suitable intensity—all measured at a distance of 10 cm from the light source. Additionally or alternatively, the suitable energy source could produce a light having a maximum peak at a wavelength of between 50-400 nm, for example between 200-280 nm (UVC), between 280-315 nm (UVB), between 315-400 nm (UVA), or between 200-400 nm. Additionally or alternatively, the suitable energy source could emit a light with a peak irradiance of between 0.1-10 W/cm², for example, between 0.3-1 W/cm², between 1.5-2.5 W/cm², or between 0.5-3.5 W/cm². Additionally or alternatively, the light produced by the suitable light source could arrive at the surface to be cured with a radiant energy density of between 0.3-8 J/cm², for example, between 1-5 J/cm², or between 1-2 J/cm².

Viewed from another perspective, the photocurable sealant component could comprise a promoter to allow polymerization within ten minutes to at least 1 on the Shore 00 hardness scale when triggered by a suitable energy source. Additionally or alternatively, the photocurable sealant component could be formulated to polymerize within ten minutes to at least 10 on at least one of the Shore A hardness scale and the Shore D hardness scale when triggered by a suitable energy source. Viewed from yet another perspective, it is contemplated that the photocurable sealant component, after polymerization triggered by a suitable energy source, could be a solid with respect to a probe.

The present inventive subject matter also provides apparatus, systems and methods in which a collection tube includes a separator substance that could maintain analyte levels (e.g., potassium levels and glucose levels) within acceptable thresholds for extended periods of time. In one embodiment, potassium levels are stable within 10% of an initial level before centrifugation and glucose levels are stable within 5%. Viewed from another perspective, one or both of the gel component and the photocurable sealant component (e.g., the entire separator substance) could be formulated to maintain a potassium level of a sample disposed in the tube within 25%, within 15%, within 10%, or even within 5% of an initial potassium level for at least four days. It is also contemplated that one or both of the gel component and the photocurable sealant component could be formulated to maintain a glucose level of a sample disposed in the tube within 25%, within 15%, within 10%, or even within 5% of an initial potassium level for at least four days, more preferably for at least five days.

Additionally or alternatively, the separator substance could advantageously be biocompatible with whole blood, and formulated to have a density between an average density of a serum/plasma fraction of whole blood and a cell-containing fraction of whole blood (e.g., about 1.04 g/cm³). The photocurable sealant component typically has a density that is slightly lower than the gel component such that, upon curing, the photocurable sealant component sits on top of the gel component and provides a clear barrier. Additionally or alternatively, the separator substance could be flowable in whole blood before curing, and immobilized after curing forming a solid layer sealant.

Viewed from another perspective, the inventive subject matter includes methods of producing sample collection tubes. A contemplated step of methods described herein could include disposing a photocurable sealant component layer material into a lumen of the tube. A further step could include disposing a gel separator component layer material into the lumen of the tube. The aforementioned steps could be completed in any suitable order such that the gel component could be disposed above or below the photocurable sealant component. In some methods, the photocurable sealant component layer material is deposited before/beneath the gel component layer material, and is configured to form a solid seal layer above the gel component layer material upon curing. In some contemplated methods, the gel component is first placed in a tube, followed by a photocurable sealant component. Upon centrifugation, the sealant component could rise above the gel component to form a seal layer that acts as a barrier between the gel component and a fraction of plasma, serum, or other sample. It should be appreciated that the gel component and the photocurable sealant component composes a composite separator substance of the inventive subject matter as described above.

Some contemplated methods could additionally comprise disposing a sample (e.g., blood) into the lumen of the tube, and centrifuging the sample collection tube with the composite separator substance and sample disposed therein. Additionally or alternatively, the sample collection tube could be exposed to a UV light (e.g., during or after centrifugation) to solidify the photocurable sealant component. Additionally or alternatively, where whole blood is disposed in the tube, a method of the inventive subject matter could comprise separating a cell-containing fraction of the whole blood from the serum fraction (e.g., by physically removing a fraction via a pipette) after exposing the tube to UV light or other suitable energy source to initiate polymerization of the photocurable sealant component.

Other optional steps of some contemplated methods include, among other things, sterilizing a collection tube before or after disposing a composite separator substance therein, and introducing a vacuum into a lumen of the tube to facilitate the draw of a predetermined volume of liquid. The step of sterilizing could be performed in any suitable manner, including for example, gamma irradiation, e-beam irradiation, or sterilizing the components by exposing to heat (e.g., to at least 250 degrees Celsius). The step of introducing a vacuum could be performed in any suitable manner. For example, an evacuation-closure device could be used to at least partially evacuate the interior of the tube and apply a stopper to the opening of the tube. Additionally or alternatively, a vacuum could be introduced into the collection tube by decompressing the volume of the lumen using any suitable pump.

It should be appreciated that a sample collection tube of the inventive subject matter could be used for fractionation of any suitable sample, including for example, whole blood. Suitable separator substances are formulated to have a suitable density intermediate to the fractions of the sample being separated. Where the sample being separated is whole blood, for example, the separator substance could be formulated to have a density between an average density of a serum fraction of whole blood and a cell-containing fraction of whole blood, and to be flowable in whole blood. Once the separator substance separates fractions of the sample being separated, the photocurable sealant component/layer can be hardened through polymerization to prevent mixing of the separated fractions.

Other components could advantageously be included in a tube of the inventive subject matter, including for example, an anticoagulant (e.g., where a sample comprises plasma) or a clot activator (e.g., where a sample comprises serum).

The inventive subject matter also provides apparatuses, compositions, systems and methods of providing polymerizable compositions that are sterilizable via irradiation or application of heat, while maintaining a predetermined flowability effective to allow sedimentation of the composition under a centrifugal force to a position between a cell-depleted phase of whole blood and a cell-enriched phase of whole blood. In some aspects, the polymerizable composition comprises an oligomer, a photoinitiator, a stabilizer and an antioxidant, and can be disposed within a lumen of a sample collection tube. Where the tube and polymerizable composition are sterilized via irradiation or heat, the predetermined flowability of the composition is preferably maintained in a manner that allows for subsequent polymerization of the composition via UV curing.

Various objects, features, aspects and advantages of the inventive subject matter will become more apparent from the following detailed description of preferred embodiments, along with the accompanying drawings in which like numerals represent like components.

DETAILED DESCRIPTION

Figure 1:
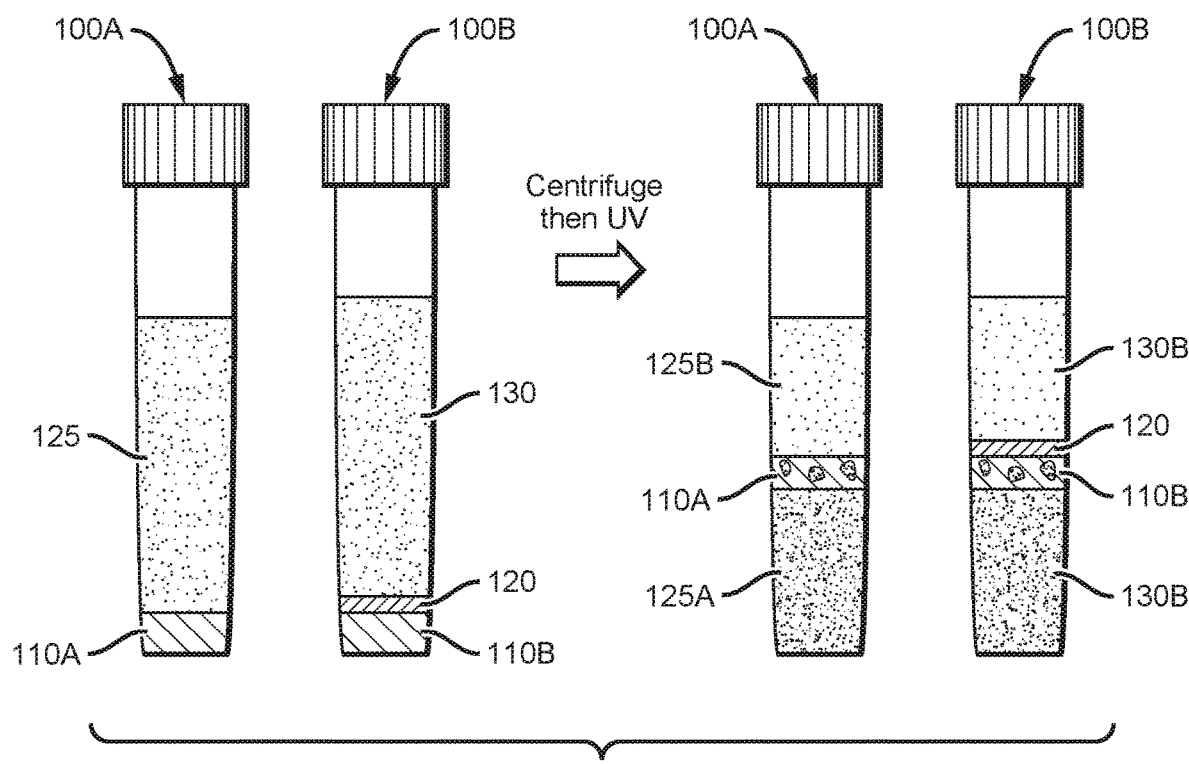
FIG. 1 illustrates a tube with a gel separator, and a tube with a composite separator before and after centrifugation and curing.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A. B, C, or D, even if not explicitly disclosed.

Separator substances of the inventive subject matter are advantageous over existing separator substances at least for the following reasons:
  Ability to separate any cell trappings that may occur within the gel from the upper test fraction.
  Reducing the UV light intensity and time exposure required for completely curing (solidifying) the barrier, at least because the volume of the photocurable sealant component required is reduced. For example, we have reduced the time required (with the same UV light intensity) from over a minute to between 10-20 seconds. This reduction has the additional benefits of decreasing the effect of UV on light-sensitive pigments, improving work flow by decreasing processing time, and decreasing exothermic heat production during curing, which may affect certain blood components such as enzymes.
  Allows for complete aspiration of a sample without substantial, if any, contamination from the gel component, at least because the solidified photocurable sealant component acts as a barrier from the gel component.
  Allows for mixing and re-mixing of a cell-free fraction of whole blood to ensure uniform sampling.
  Prevents remixing of blood that can occur when soft gel separators are physically disrupted by agitation, for example, during shipping or mixing.
  Allows for repeated freeze/thaw cycles of the tube. Freezing of serum or plasma is common practice, for example, for future testing or for compliance with certain regulatory requirements. Where a gel separator is used to separate fractions of a sample, the fraction below the separator will typically freeze before the gel, thereby expanding and distorting the shape of the gel separator barrier. Since a separator substance of the inventive subject matter includes a photocurable sealant component that is formulated to solidify upon exposure to a suitable energy source, some or all of the problems typically associated with freezing and thawing separator tubes are significantly reduced or even eliminated.
  The photocurable layer can be minimized in volume thereby reducing cost.
  The photocurable layer does not need to be thixotropic since thixotropic soft gel is loaded into the tube above the photocurable layer and no flow will result prior to use. This allows for simple compositions with less cell trapping, and eliminates the need for additives that may contribute to degrading blood cells or interference with lab assays.
  Decreases labor costs associated with removing serum or plasma to a secondary tube.
  Decreases potential for re-labeling errors associated with removing serum or plasma to a secondary tube.

Feasibility has been demonstrated using a photocurable sealant comprising: (1) at least one of a monomer, and an oligomer (e.g., a combination (e.g., Ebecryl, Cytec) thereof), with (2) a photoinitiator (e.g., Additol) BDK, Additoli TPO) and (3) a stabilizer (phenothiazine). It should be appreciated that any commercially suitable photocurable sealant component can be used. Suitable photocurable sealant components are typically at least one of a gel (e.g., when a gelling agent is added (e.g., DBS or silica)) and flowable (with whole blood) prior to polymerization, and can solidify when exposed to a suitable energy source (e.g., UV light).

Examples of suitable photocurable sealants can include, among other things, MLA (e.g., MILA1), MLAI (e.g., MILIA1 and phenothiazine), MAI (e.g., MIA1 and phenothiazine), LAI (e.g., LIA1 and phenothiazine), and LMA (e.g., LIMIA1). As used herein, M=a monomer (e.g., M1, which is a monomer Trimethylolpropane propoxylate triacrylate from Sigma-Aldrich Cat. No. 407577); L=an oligomer (e.g., L1=Ebecryl 230 from Allnex, previously from Cytec Industries, Inc.); A=a photoinitiator (e.g., A1=Additol BDK); I=a stabilizer (e.g., phenothiazine). See Table 1 below. LAI (e.g., L1, A1 and phenothiazine) can be included in some especially preferred photocurable sealant components, as it can have the desired density range of 1.00-1.09 g/cm$^3$.

Other examples of suitable photocurable sealants include LAIR, LAIE (e.g., L1, A1, phenothiazine and tocopherol), and LAIER, wherein R=a gelling agent (e.g., DBS, silica), and E=at least one of an antioxidant and a radical scavenger (e.g., Vitamin E, butylated hydroxytoluene (BHT), butylated hydroxyanisole (BHA), carotene, bilirubin, ascorbic acid). While R and E are generally not necessary, each can provide advantageous features to the photocurable sealant. More specifically, a gelling agent is generally not a necessary component of the photocurable sealant because a thixotropic soft gel can be loaded into the tube above the photocurable layer such that no flow will result prior to use. Nonetheless, it may be desirable to have a thixotropic sealant, for example, where it is desirable to have the sealant disposed in the tube on top of the soft gel component. Additionally, a radical scavenger such as compounds having Vitamin E activity (e.g., tocopherol), while not necessary, can allow the photocurable sealant to be sterilized via irradiation (e.g., gamma, e-beam) without curing (e.g., by changing the density properties), rather than requiring heat sterilization to maintain a flowability effective to allow sedimentation between two fractions of a sample.

TABLE 1

| ABBREVIATION | NAME |
|---|---|
| R | Gelling Agent (e.g., DBS, silica) |
| M | Monomer |
| M1 | Trimethylolpropane propoxylate triacrylate |
| L | Oligomer |
| L1 | Ebecryl 230 from Allnex |
| A | Photoinitiator |
| A1 | Additol BDK |
| I | Stabilizer |
| I1 | Phenothiazine |
| E | Antioxidant/radical scavenger (e.g., Vitamin E, BHT, BHA, carotene, bilirubin, ascorbic acid) |
| D | Density adjuster (e.g., Ebecryl 113 from Cytec) |

It is contemplated that composite separators of the inventive subject matter, in one or both of the photocurable and gel components, could include a polymer such as silicon oil, polyamides, olefinic polymers, polyacrylates, polyesters and copolymers thereof, polysilanes and polyisoprenes. Additionally or alternatively, composite separators could include a filler (e.g., silica, latex, other inert material) to adjust a density of the separator or component thereof. Additionally or alternatively, composite separators could include additional materials or reagents to achieve a desired purpose (e.g., EDTA (chelating agent), or heparin, citrate, dextrose (anticoagulants)).

Similarly, it should be appreciated that any suitable gel component can be disposed in a tube of the inventive subject matter. Suitable gel components include those that liquefy during centrifugation and re-gel thereafter, and can include, for example, off the shelf gels (e.g., BD Vacutainer® SS™, BD Vacutainer® PST™, Vacuette® blood collection tubes with gel separators, PPMA serum separator gel tubes. Polypropylene serum separator gel tubes), or any other commercially suitable gel that is formulated to, upon centrifugation, be located between two fractions of a sample (e.g., between a serum and a blood clot, between serum and cell containing fraction of whole blood).

FIG. 1 illustrates a control tube 100A and a tube of the inventive subject matter 100B. Control tube 100A is a sample collection tube (e.g., Vacutainer) including a commercially available gel separator 110A. Tube 100B is a sample collection tube including a commercially available gel separator 110B, and a photocurable sealant 120. A sample of whole blood 125 is transferred into control tube 100A, and another sample of whole blood 130 is transferred into control tube 100B. Upon centrifugation, gel separator 110A (including some cells trapped from the cell-enriched fraction) is positioned between a denser fraction of whole blood 125A, and a less dense fraction of whole blood 125B in tube 100A. Gel separator 110B (including some cells trapped from the cell-enriched fraction) is similarly positioned between denser and less dense fractions of whole blood, 130A and 130B, respectively.

Advantageously the photo-sealant 120, which includes no gelling agents or thixotropy-modifying constituents, is clear and free of cell trapping before and after each of centrifugation and UV curing in tube 100B. Cell trapping is undesirable because of analyte leach into the test fraction. Cells frequently adhere to the upper layer of soft gels such as 110A and 110B as shown in FIG. 1. However, they can be separated from the plasma by the photo-sealant 120.

The following data shows improved analyte stability using a composite separator of the inventive subject matter (photogel plasma separator tube) when compared to using a soft gel alone.

| | BD Plasma Separator Tube | | | | Photogel Plasma Separator Tube | | | |
|---|---|---|---|---|---|---|---|---|
| Comprehensive Metabolic Panel | Immediate Spin | 24 Hours | 5 Days | Freeze/ Thaw | Immediate Spin | 24 Hours | 5 Days | Freeze/ Thaw |
| sodium mEq/L | 142 | 139 | 140 | 143 | 140 | 140 | 142 | 143 |
| potassium mEq/L | 3.7 | 3.7 | 4.1 | 4.5 | 3.6 | 3.6 | 3.7 | 3.8 |
| chlorides mEq/L | 106 | 104 | 105 | 108 | 106 | 105 | 107 | 108 |
| CO2 mEq/L | 29 | 27 | 26 | 22 | 27 | 25 | 25 | 22 |
| glucose mg/dL | 102 | 100 | 93 | 91 | 104 | 105 | 102 | 106 |
| urea nitrogen mg/dL | 16 | 15 | 16 | 16 | 17 | 16 | 16 | 16 |
| creatinine mg/dL | 0.6 | 0.8 | 0.8 | 0.8 | 0.7 | 0.8 | 0.8 | 0.5 |
| calcium mg/dL | 9.4 | 9.3 | 9.5 | 9.7 | 9.2 | 9.4 | 9.5 | 9.6 |
| total protein g/dL | 6.8 | 6.8 | 6.4 | 7 | 6.8 | 7 | 6.7 | 7 |
| albumin g/dL | 4 | 4 | 4 | 4 | 4 | 4.1 | 4.1 | 4 |
| alk phos IU/L | 37 | 39 | 36 | 38 | 36 | 38 | 39 | 37 |
| AST IU/L | 17 | 15 | 19 | 26 | 17 | 17 | 18 | 16 |
| ALT IU/L | 15 | 16 | 19 | 16 | 16 | 17 | 17 | 13 |
| bilirubin mg/dL | 0.6 | 0.7 | 0.6 | 0.5 | 0.5 | 0.6 | 0.6 | 0.4 |

Some sample collection tubes of the inventive subject matter can comprise a tube, plug, and a separator substance having a gel component/layer and a photocurable sealant component/layer disposed in a lumen of the tube. The collection tube can be manufactured out of a suitably rigid material to support a vacuum within the lumen. Example materials include hard plastics, glass, or other similar materials. The lumen is preferably of sufficient volume to hold a desirable sample of whole blood or other liquid. Typical volumes range from a few ml to 10 ml or greater. The plug could fit sufficiently snug into the tube to maintain the vacuum within lumen. An example of an acceptable tube that can be used to produce a collection tube of the inventive subject matter includes the Vacutainer® specimen collection products developed by Becton, Dickenson and Company (Franklin Lakes, N.J. USA 07417).

The term "tube" is used euphemistically to refer to vessels having a cavity. Although a preferred embodiment includes a tube, one should appreciate that other vessels having a cavity can also be used while still falling within the scope of the inventive subject matter. For example, it is contemplated that collection tube could be replaced with other vessels that can contain a liquid or optionally support a vacuum. Alternative examples of vessels include flasks, jars, beakers, bottles, blood collection bags, or phials. Vessels beyond mere tubes also have utility when the inventive subject matter is applied to alternative markets beyond blood collection.

In a preferred embodiment, a collection tube is produced by disposing a composite separator within a lumen of the tube, and introducing a vacuum within the lumen in preparation for sale. It can be preferred (e.g., for cost and cure time purposes) that no more than about 1 ml, or about 1 gram, of the separator substance is disposed into the lumen for a typical 10 ml collection tube. Additionally or alternatively, it can be preferred that no more than 50%, more preferably no more than 25%, and even more preferably no more than 10% of the separator substance comprises the photocurable sealant layer. It is contemplated that other amounts of the separator substance (or layer thereof) could be used in some embodiments to fit a specific use case. For example a smaller version of a tube could require less of a separator substance, while a larger version might require more to make an adequate sealed barrier.

In some embodiments, collection tubes are sterilized to satisfy the International Organization for Standardization (ISO) protocols before being sold. For example, tubes can be sterilized (preferably without substantial polymerization of the separator substance or portion thereof) using gamma radiation (e.g., from a Cobalt source (e.g., Colbalt 60)), using e-beam radiation (e.g., from an e-beam generator), gas (e.g., ethylene oxide), or a heat between 100 to 250 degrees Celsius or even more. Viewed from another perspective, the separator substance can be effective to allow irradiation, gas, or heat sterilization without curing more than 40%, more preferably without curing more than 30%, and to allow subsequent polymerization via UV or other curing. An optional vacuum can be introduced, for example, by simply decompressing the volume of the tube's lumen by using a suitable pump.

All suitable sterilization times are contemplated (e.g., less than 10 minutes, less than 5 minutes, less than 2 minutes, between 5-120 seconds, between 5-90 seconds), where the collection tubes (and separator substances) are e-beam sterilized at dosages of between 5-25 kGy, more typically between 10-20 kGy. All suitable sterilization times are contemplated (e.g., less than 10 minutes, less than 5 minutes, less than 2 minutes, between 5-120 seconds, between 5-90 seconds), where the collection tubes (and separator substances) are gamma sterilized at dosages of between 5-25 kGy, more typically between 10-20 kGy. It has been observed that with gamma sterilization, weaker sources with lower dose delivery rates were more likely to cure the compound. The dose required by the ISO depends on, among other things, the bioburden of the object being sterilized. The radiation time required depends on not only the sterilization technique used, but also, for example, the bioburden of the object being sterilized, and the radiation dose (kGy).

It is also contemplated that a collection tube could be sterilized, and a sterilized separator substance could be added to the tube. Additionally or alternatively, a user could add one or more separator substances to a collection tube after purchase, as opposed to having a separator substance pre-disposed within the tube.

Where a sample (e.g., whole blood) is added to a collection tube of the inventive subject matter, centrifugation could separate the whole blood into a serum fraction and a cell-containing fraction. When each layer (gel/photocurable sealant) of the separator substance has a density that is intermediate to that of serum faction and cell-containing fraction, it can migrate between the two fractions during centrifugation, thereby isolating the fractions from each other. The separator substance can then be rapidly hardened through polymerization when triggered by a suitable energy source to provide a solid barrier between the two fractions.

As discussed above, the suitable light source could emit a light having an intensity of between 5-100 $W/cm^2$, between 10-75 $W/cm^2$, between 15-50 $W/cm^2$, or any other suitable intensity. Additionally or alternatively, the suitable energy source could produce a light having a maximum peak at a wavelength of between 50-400 nm, for example between 200-280 nm (UVC), between 280-315 nm (UVB), between 315-400 nm (UVA), or between 200-400 nm. Additionally or alternatively, the suitable energy source could emit a light with a peak irradiance of between 0.1-10 $W/cm^2$, for example, between 0.3-1 $W/cm^2$, between 1.5-2.5 $W/cm^2$, or between 0.5-3.5 $W/cm^2$. Additionally or alternatively, the light produced by the suitable light source could arrive at the surface to be cured with a radiant energy density of between 0.3-8 $J/cm^2$, for example, between 1-5 $J/cm^2$, or between 1-2 $J/cm^2$.

One exemplary suitable light source is a custom light box made by Heraeus that produces a light having a maximum peak at a wavelength of 385 nm, and a peak irradiance of 2.2 $W/cm^2$. This light source was used with a power setting of 25% of maximum optical output power of 25 W. Some of the tested photocurable substances had a volume of between 0.25-1 mL, was disposed in vacutainer tubes, and the suitable energy sources were light emitting diodes emitting energy at between 380-390 nm, with a peak irradiance of 2.2 $W/cm^2$. However, it should be appreciated that one or more factors of exposure (e.g., irradiance, wavelengths, radiant energy) can be modified, concentrations of substance components could be modified (e.g., antioxidant concentration, photoinitiator concentration), or different energy sources could be used, to achieve a similar cure time for smaller or larger volumes.

Figure 2:
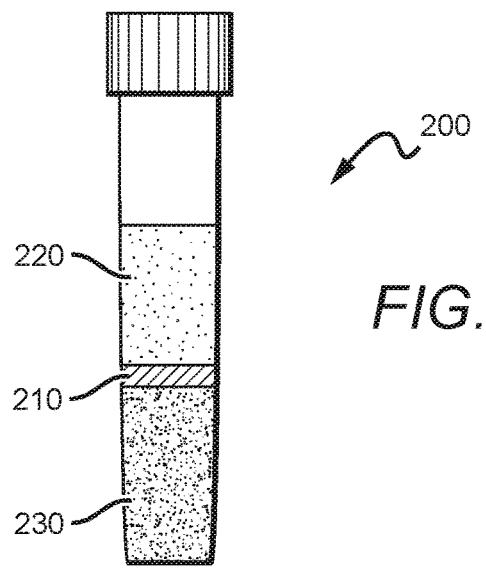
FIG. 2 illustrates a separator tube comprising a photopolymer separator of the inventive subject matter.

In some aspects of the inventive subject matter, a separator tube can be provided with (1) both a polymerizable composition and a thixotropic gel, as shown in FIG. 1, or (2) a polymerizable composition alone, as shown in FIG. 2. As illustrated, sample collection tube 200 comprises a polymerizable composition 210 of the inventive subject matter (e.g., LAIE) disposed therein and cured after centrifugation to a position between a cell-depleted phase 220 and a cell-enriched phase 230 of whole blood.

The polymerizable composition preferably comprises at least three of the following components: an oligomer (L) (e.g., an acrylate containing oligomer and a methacrylate containing oligomer), a photoinitiator (A), a stabilizer (I) and at least one of a radical scavenger and an antioxidant (E).

The polymerizable composition can advantageously have a composition effective to allow irradiation sterilization (e.g., gamma, e-beam) without loss of a predetermined flowability (e.g., effective to allow sedimentation of the composition under a centrifugal force to a position between two phases of a sample (e.g., a cell-depleted phase and a cell-enriched phase of whole blood)).

Viewed from another perspective, the composition can be effective to allow irradiation or heat sterilization without curing the composition more than 40%, more preferably without curing the composition more than 30%, and to allow subsequent polymerization via UV or other curing.

The subsequent polymerization via UV curing could occur minutes (e.g., more than 30 minutes), hours (e.g., more than 1 hour, more than 2 hours, more than 5 hours, more than 10 hours), days (more than 1 day, more than 5 days, more than 10 days, more than 15 days, more than 20 days, more than 25 days), months (more than 1 month, more than 2 months, more than 6 months, more than 9 months) or even years (more than 1 year, more than 2 years, more than 3 years, more than 5 years or even longer) after irradiation sterilization occurs. In some embodiments, the polymerizable composition can be subject to a radiation dose of between 5 and kGy, inclusive, more preferably a radiation dose of between 10 and 30 kGy, inclusive, and even more preferably a radiation dose of between 10 and 20 kGy, inclusive, without loss of the flowability. Viewed from a different perspective, the polymerizable composition can be subject to a radiation dose of less than 30 kGy, more preferably less than 20 kGy, and even more preferably less than 17 kGy to both (1) allow irradiation sterilization without loss of the predetermined flowability, and (2) allow subsequent polymerization via UV curing.

It is contemplated that a photoinitiator (e.g., Azobisisobutyronitrile, Benzoyl peroxide, Camphorquinone, a phosphine oxide photoinitiator, a ketone-based photoinitiator, a benzoin ether photoinitiator) could be present in the polymerizable composition in any suitable concentration. In some preferred embodiments, the photoinitiator is present in the composition in a concentration of less than 5 wt %, more preferably in a concentration of less than 2 wt %, and even more preferably in a concentration of less than 1.5 wt %. Additionally or alternatively, a polymerizable composition of the inventive subject matter could comprise a photoinhibitor.

It should be noted that a radical scavenger or antioxidant is not necessary in all contemplated polymerizable compositions. However, where included (e.g., to facilitate maintaining flowability through irradiation sterilization via gamma beam or electron beam), it is contemplated that the at least one of the radical scavenger and the antioxidant (e.g., tocopherol) can be present in the polymerizable composition in any suitable molar concentration. Applicant surprisingly found that where a radical scavenger such as tocopherol is included, some compositions of the inventive subject matter (e.g., LAIE) will maintain flowability during irradiation sterilization at a radiation dosage of more than 3 kG, while some other compositions (e.g., LAI) will not maintain flowability under the same radiation dosage. Viewed from another perspective, LAI was found to only maintain flowability during irradiation sterilization up to a radiation dosage of approximately 3 kG. In some preferred embodiments, the at least one of the radical scavenger and the antioxidant comprises tocopherol and is present in the composition in a molar concentration of at least 75 mM, more preferably at least 100 mM, and even more preferably at least 135 mM. Lower concentrations of tocopherol (e.g., less than about 75 mM) are not preferable for various reasons. For example, separator substances with lower tocopherol concentrations can only maintain flowability at lower radiation dosages, which may not allow for cost-effective sterilization under the ISO protocol. Additionally, separator substances with lower tocopherol concentrations typically require lower photoinitiator concentrations (e.g., less than 1 wt %), which generally requires a longer cure time.

Additionally or alternatively, the polymerizable composition could be polymerizable by UV curing (e.g., after irradiation sterilization (gamma, e-beam)) to form any suitable polymer, including for example, an acrylate polymer, a methacrylate polymer, an epoxy polymer, a polyurethane, or a thiol-ene polymer.

Viewed from a different perspective, a polymerizable composition of the inventive subject matter could comprise one or more of a polymer containing a terminal epoxy group, a polymer containing a pendant epoxy group, an epoxy-siloxane resin, an epoxy-polyurethane, an epoxy-polyester, epichlorohydrin, a polyhydric diol, a polyhydric polyol, a polymer comprising a terminal or pendant isocyanate group, a polymer comprising at least two hydroxyl groups, a polyhydric diol, a polyhydric polyol, an aliphatic monomeric polythiol, an aliphatic dithiol, an aromatic dithiol, a polymeric polythiol, an acrylate, a methacrylate, an alkenyl, and a cycloalkenyl. Where a polymerizable composition of the inventive subject matter is subject to a suitable energy source (e.g., a UV energy source), it is contemplated that the composition can be cured to a hardness of at least 1 (e.g., a hardness of at least 10) on a Shore A hardness scale over a period of less than ten minutes, more preferably a period of less than 5 minutes, more preferably a period of less than 60 seconds, and even more preferably, a period of less than 20 seconds. Viewed from another perspective, it is contemplated that the composition can be cured to a hardness of at least 1 (e.g., a hardness of at least 10) on the Shore 00 hardness scale within at least 10 minutes, more preferably a period of less than 5 minutes, more preferably a period of less than 60 seconds, and even more preferably, a period of less than 20 seconds. Viewed from yet another perspective, it is contemplated that the composition can be cured to a hardness of at least 1 (e.g., a hardness of at least 10) on a Shore D hardness scale over a period of less than ten minutes, more preferably a period of less than 5 minutes, more preferably a period of less than 60 seconds, and even more preferably a period of less than 20 seconds.

Experiments

Various candidate compositions variably comprising an oligomer or a monomer (or both), a photoinitiator, a stabilizer, an antioxidant, a density adjuster or gelling agent (or both) were tested to determine, among other things, whether a predetermined flowability could be maintained during irradiation (e-beam or gamma) sterilization at various radiation dosages and for various time periods. More specifically, the compositions were tested with respect to the following:
  a. Final Density—tested by pycnometry and performance in whole blood during centrifugation. The final density of some preferred compositions was between 1.04-1.08 g/cm$^3$.
  b. Interference with lab tests—tested by comparing results to those obtained in blood collected in BD tubes. No interference was inferred when the means of the measurements were within assay CVs. The lab test comparison included the whole process of using the separator in the centrifuge and curing with UV. Monomers and oligomers were also tested with respect to leaving the blood in contact with the cure photopolymer for up to 8 days looking for delayed interference.
    i. Comprehensive metabolic panel (sodium, potassium, chloride, CO2, creatinine, bilirubin (direct and total), total protein, AST, ALT, alkaline phosphatase, glucose, urea nitrogen, albumin)
    ii. Immunoassays (PSA, testosterone, estradiol, TSH, thyroxine (free T4), ferritin, sensitive CRP)
    iii. Electrophoresis (serum protein electrophoresis and immunofixation (fraction quantitation (5 fractions), paraprotein identification), lipid panels by electrophoresis)

iv. Lipids (total cholesterol, LDL-c, HDL-c, VLDL-c, Lp(a), triglycerides)
v. Molecular tests (DNA (braf), exosome RNA (HBB, ACTB, DEFA3), GAPDH, ITGA2B))
vi. Therapeutic drug monitoring (amikacin, primadone, lidocaine, caffeine, acetaminophen, NAP, procainamide)
vii. Platelet, red cell and white cell counts (with differentials) in plasma, including platelet aggregation to ristocetin, collagen, and ADP.
c. Less interference was observed with one or more of i-vii above when the amount of photopolymer or gel separator was reduced. The components of either have the potential for interference. When a specific analyte is interfered with by the gel component, that component can be reduced. When a specific analyte is interfered with by the photopolymer component, that component can be reduced.
d. Hemolysis—measured by index on automated analyzers, visual assessment and elevate potassium levels.
e. Cure times with UV lamps (arc lamps, microwave power bulbs, LEDs)
   i. Increasing antioxidant concentration beyond (for example over 500 mM tocopherol) adversely affects cure times (prolongs). Increasing the photoinitiator concentration beyond approximately 3% to offset this effect adversely affected the function of the antioxidant in preserving the compound through sterilizing irradiation.
f. Heat production when cured.
g. Shrinkage when cured.
h. Ability to be sterilized by heat or irradiation (ebeam and gamma at various doses and dose delivery schema).
   i. For heat sterilization, no antioxidants were required and several combinations of L and M satisfy the other performance requirements.
   ii. For sterilization by irradiation, a given composition is more likely to work if the dose is delivered quickly (for example by ebeam rather than by gamma).
      1. LAI can be sterilized with up to 3 kGy without an antioxidant.

The monomers tested (some in combination for density adjustment) included M1, 1,6 hexanediol ethoxylate diacrytale, Poly(ethylene glycol) methyl ether methacrylate, Poly(ethylene glycol) diacrylate (Cat. No. 437441), Poly (ethylene glycol) diacrylate (Cat. No. 475629), Trimethylolpropane propoxylate triacrylate, and 1,6-Hexanediol ethoxylate diacrylate (Cat. No. 497134). Of the monomers tested, M1 worked best. Unfortunately, compositions including one or more monomers (e.g., M1) resulted in shrinkage after curing and were therefore not considered optimal for use in sealant compositions. However, it is contemplated that the compositions could be modified, for example, to address the cure rate and temperature produced to prevent or reduce shrinkage.

The oligomers tested were all in the Ebecryl series, and included L1-L10 (various oligomers obtained from Cytec). Of the oligomers tested, L1, L2, L6, L8, L9 and L10 were better suited for maintaining flowability compared to L3-L5 and L7. L1 performed the best with respect to, for example, less heat generation during curing, less shrinkage (if any), density, viscosity, less bubble trapping, and less interference exhibited using standard serum tests, and the other oligomers were abandoned for failing to meet the criteria. L8 and L9 resulted in greater interference with enzymes than L1, while L10 resulted in visible interaction with cured materials. The plasma visibly dissected into the top layer of the barrier.

Although L1 had the best overall performance of the oligomers tested in the Ebecryl series, it should be appreciated that several oligomers were able to maintain flowability during irradiation sterilization. It should also be appreciated that adjustment, for example, to a radiation dosage, sterilization time, or concentration of a constituent of the photocurable substances could be made by a person having ordinary skill in the art to allow various other oligomers to be included in a separator substances formulated to maintain flowability during irradiation sterilization.

The photoinitiators tested in 1 wt % concentration in M1, included (Azobisisobutylonitrile): 254 nm; Benzophenone: 254 nm; 4-(Dimethylamino)benzophenone: 356 mu; 4,4'-Bis(dimnethylamino)benzophenone: 370 mu; 4,4'-Bis(diethylamino)benzophenone: 379 nm; and A1: 365 nm. The wavelength of photoinitiator was chosen by transmission through PET tubes that would be used. A1 was found to have superior performance, using criteria including, compatibility with blood, cure times, heat generation, and miscibility with oligomers and monomers. Some of the other photoinitiators could be used, for example, with a greater cure time or a different light source.

A1 was tested in various concentrations in L1 (between 0.5-8 wt %, inclusive). 1%±0.5% was found to be optimum where antioxidant(s) were present. However, the concentration of A1 could be increased up to approximately 3% without adversely affecting the function of vitamin E. Additol TPO, which has a longer wavelength absorption to match selected UV sources, was also tested in various concentrations in L1. When Additol TPO was tested in 1% concentration with L1, I1 and vitamin E in 200-300 mM concentration, the cure time was somewhat better than when A1 was tested in 1% concentration with L1, I1 and vitamin E in 200-300 mM concentration. Furthermore, no interference was seen using a comprehensive metabolic panel.

The stabilizer tested is Phenothiazine in 0.1 wt % concentration. This stabilizer was present in all samples. However, it is contemplated that any suitable stabilizer at any suitable concentration could be used, including for example, suitable stabilizers that would work in an evacuated (low $O_2$) atmosphere.

The antioxidants tested included alpha-tocopherol—2 mM-500 mM, carotene, bilirubin, BHT, BHA, tempo, and 4-OH-tempo. While tocopherol, tempo and 4-OH-tempo each maintained flowability during irradiation in dosages above 15 kGy (carotene, bilirubin, BHT and BHA failed), Tempo and 4-OH-tempo caused hemolysis and lab interference. Tempo, however, was able to maintain flowability during irradiation in dosages of up to 37 kGy, and no heat step was required. Tocopherol was found to have the best performance.

The density adjusters tested included Ebecryl 113 from CYTEC. A physical gel formulation denoted LARID (D=Ebecryl 113 from Cytec) was tested and shown to have a good cure time and little or no interference with most lab tests. LARID comprises:
a. 30% L=EBECRYL 230 and 70% D
b. wherein:
   i. 1% (of L+D) A1 (Additol BDK);
   ii. 8.19% (of L+D) R, fumed silica R1 (AEROSIL R805 from Degussa); and
   iii. 0.1% (of L+D) I (Phenothiazine from Sigma).

The LARID formulation was found to be non-sterilizable by irradiation (while maintaining flowability) because no antioxidant was present.

1 The gelling agents tested included fumed silica and DBS (1,3:2,4-dibenzylidene sorbitol) and cosolvent NMP (N-Methylpyrrolidone). DBS performed worse than silica in terms of sterilization by irradiation while maintaining flowability. With 0.6% DBS and 1.8% NMP, the L1A1I1 system gels. It is shear thinning and has a density lower than a BD gel. The UV curing time was about the same as L1A1I1R1 and the cured gel was able to survive one round with a liquid nitrogen-hot water test, which means the cured gel could survive many rounds of freeze-thaw cycles.

EXAMPLES

The following experimental data is provided to exemplarily illustrate various aspects of the inventive subject matter presented herein. More specifically, the data illustrates the surprising effects of tocopherol and Additol BDK at specified concentrations in maintaining flowability of a composition (to allow for sedimentation between two phases of whole blood upon centrifugation) after irradiation sterilization at specified radiation dosages. As shown, compositions comprising an oligomer (EBECRYL 230), a photoinitiator, Additol BDK, in a concentration of less than 2 wt %, and a radical scavenger (tocopherol, in a concentration of at least 75 mM) surprisingly maintained flowability after irradiation sterilization (gamma or e-beam) at a dosage of less than 20 kGy. Where lower concentrations of tocopherol or photoinitiator were present, radiation protocols could be modified (e.g., to require a higher dose rate (e-beam), post-sterilization heat, and lower dosages (kGy), longer cure times). Where amounts lower than about 60 mM tocopherol were present, it was generally observed that the total dose deliverable was lower, making the sterilization protocols not feasible. In contrast, compositions lacking a radical scavenger and compositions having a photoinitiator concentration of greater than 3 wt % (e.g., greater than 5 wt %) were unable to maintain flowability after irradiation sterilization.

| Composition | Tocopherol Conc. (mM) | Photo-initiator Conc. (wt %) | Dose (kGy) | Sterilization Method | Post-Sterilization Heat | Pass (maintain flowability) or Fail | Cure Time |
|---|---|---|---|---|---|---|---|
| L1A1I1-DBS (L1A1I1 = Ebecryl 230, Additol BDK, phenothiazine) (DBS = dibenzylidene sorbitol) | 0 | 1 | 3-5 | Gamma | None | Fail (Failed worse with increased DBS) | |
| L1A1I1 | 0 | 1 | 17 | e-beam | None | Fail | |
| L1A1I1 | 0 | 1 | 15 | Gamma | None | Fail | |
| L1A1I1 | 0 | 1 | 10 | Gamma | None | Fail | |
| LARID | 140 | 1 | 16 | e-beam | None | Fail | |
| LAIE (Ebecryl 230, Additol BDK, phenothiazine, tocopherol) | 0.1-2.0 | 1 | 25 | Gamma | None | Fail | |
| LAIE | 10, 20 | 1 | 25 | Gamma | None | Fail | |
| LAIE | 75 | .5 | 15 | e-beam | None | Fail | |
| LAIE | 75 | 1 | 15 | e-beam | 60-70 C. 60 min | Fail | |
| LAIE | 75 | .5 | 10 | e-beam | 60-70 C. 60 min | Pass | Typically <5 minutes |
| LAIE | 100 | 1 | 12 | e-beam | 60-70 C. 60 min | Pass | Typically <1 minute |
| LAIE | 120 | 1 | 15 | e-beam | 60-70 C. 60 min | Pass | Typically <1 minute |
| LAIE | 120 | 1 | 16.1 | Gamma | 70 C. 60 min | Fail | |
| LAIE | 100, 120, 140 | 1 | 16.1 | e-beam | None | Almost | |
| LAIE | 140 | 1.5 | 12 | e-beam | 60-70 C. 60 min | Pass | Typically <1 minute |
| LAIE | 140 | 1 | 16.1 | e-beam | 70 C. 60 min | Pass | Typically <1 minute |
| LAIE | 140-200 | 2-5 | 15-20 | e-beam or Gamma | None | Fail | |

-continued

| Composition | Tocopherol Conc. (mM) | Photo-initiator Conc. (wt %) | Dose (kGy) | Sterilization Method | Post-Sterilization Heat | Pass (maintain flowability) or Fail | Cure Time |
|---|---|---|---|---|---|---|---|
| LAIE | 140 | 2-3 | 17 | e-beam | None | Fail | |
| LAIE | 140 | 1 | 16 | e-beam | None | Close | |
| LAIE | 140, 200 | 1 | 16 | e-beam | 60-70 C. 60 min | Pass | Typically <1 minute |
| LAIE | 145 | 1 | 16 | e-beam | 50 C. 2 hours | Fail | |
| LAIE | 145 | 1 | 12 | e-beam or Gamma | 70 C. 60 min | Pass | Typically <2 minutes |
| LAIE | 145 | 1 | 16 | e-beam or Gamma | 70 C. 60 min | Pass | Typically <2 minutes |
| LAIE | 200 | 5 | 15-20 | e-beam or Gamma | None | Fail | |

As illustrated herein, a technical effect of some aspects of the inventive subject matter is that tocopherol included in a sealant composition in a suitable concentration range (e.g., between 75-200 mM, between 75-150 mM, between 100-150 mM, between 100-250 mM, between 125-350 mM) can both (1) scavenge or interfere with radicals produced during irradiation (e.g., e-beam or gamma) sterilization, and (2) not scavenge or interfere with radicals produced during UV induced polymerization. Viewed from a different perspective, tocopherol must be present in an amount that is effective to prevent runaway polymerization when radicals are produced during e-beam or gamma sterilization, but not effective to prevent polymerization in the presence of UV or other suitable source of energy.

In some embodiments of the inventive subject matter, two types of radical scavengers are included in a separator composition. A first radical scavenger (e.g., E) can be sensitive to radicals that trigger polymerization that are produced by ebeam or gamma irradiation. A second radical scavenger (e.g., I) can be sensitive to radicals that trigger polymerization that are produced by a photoinitiator. Therefore, while not wishing to be bound by any particular theory or limit the scope of the inventive subject matter, a technical effect of some aspects of the inventive subject matter is that E (e.g., tocopherol) can be used to maintain a proper balance between A (photoinitiator) and I (stabilizer) required for hardening of L (oligomer) in the presence of irradiation induced formation of radicals. In other words, if there was an increase in I in an amount appropriate to scavenge radicals during irradiation sterilization (above 3 kG), the I in the composition would overwhelm A, and the composition would not cure upon exposure to a UV energy source. Compositions of the inventive subject matter could comprise I in a lower amount that allows for curing/hardening of the composition upon exposure to a UV energy source because of the presence of E. Viewed from another perspective, the E can be considered a sacrificial antioxidant that can be dispensed with, and that does not interfere with a polymerization reaction induced by A.

While not wishing to be bound by any particular theory, it is also contemplated that in some embodiments, a stabilizer I may not be necessary to allow for irradiation sterilization and separate UV curing. Experiments have shown that LAI does not maintain flowability when sterilized via irradiation. However, it is contemplated that an LAE composition can maintain flowability during irradiation sterilization to allow for subsequent UV curing when E is included in a concentration that is not effective to consume radicals generated by A, but effective to consume radicals generated during irradiation sterilization.

While the above data is based on L being L1, it should be appreciated that other oligomers (e.g., an acrylate containing oligomer and a methacrylate containing oligomer) are expected to work in place of L1 because of their similar chemical makeup and use in free radical polymerization. Similarly, while the above data is based on A being A1 (Additol BDK), other photoinitiators are expected to work in place of A1 (e.g., a phosphine oxide photoinitiator, a ketone-based photoinitiator, and a benzoin ether photoinitiator) because of their ability to decompose into free radicals when exposed to light, and ability to promote polymerization reactions.

Additionally or alternatively, other stabilizers could be used in place of phenothiazine (e.g., hydroquinone) as they would be expected to similarly prolong storage and shelf life of the composition. Other radical scavengers are also expected to work in place of tocopherol; however, other radical scavengers tested (e.g., BHA, BHT, carotene, ascorbic acid, bilirubin, gallic acid, and tempo nitroxide) were shown to interfere with some lab tests. Nonetheless, these scavengers can be used if the types of tests used are limited to specific clinical laboratory tests. For example, certain antioxidants were found to interfere with the measurement of some immunoassays but not with molecular testing.

Based on the information provided herein, it is contemplated that a person skilled in the art would be able to adjust radiation or other parameters such that flowability of a separator substance having different constituents and concentrations thereof could be maintained during irradiation sterilization, and such that the substance could subsequently be UV cured. For example, the PHOSITA should appreciate that a given composition is more likely to maintain flowability during irradiation sterilization where the dose is delivered quickly (e.g., e-beam vs. gamma). Additionally, the PHOSITA should appreciate that increasing antioxidant concentration (e.g., above 500 m) prolongs cure times, and that increasing photoinitiator concentration to offset this effect (e.g., above 3%0) adversely affects the function of the antioxidant in preserving the separator substance through sterilization irradiation.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A sample collection tube, comprising:
    a tube having a lumen; and
    a flowable polymerizable composition disposed within the lumen and having a density of between 1.00-1.09 g/cm3 such that it sediments the composition under a centrifugal force to a position between a cell-depleted phase of whole blood and a cell-enriched phase of whole blood when disposed in the lumen with whole blood;
    wherein the polymerizable composition comprises:
    an oligomer;
    a photoinitiator present in a concentration of less than 5 wt % of the polymerizable composition, which when exposed to UV light causes the polymerizable composition to harden;
    a stabilizer; and
    tocopherol present in the polymerizable composition at a concentration between 75 and 350 mM; and
    wherein the polymerizable composition maintains a density of between 1.00-1.09 g/cm3 during and after the sample collection tube containing the polymerizable composition has been exposed to irradiation sterilization, and following irradiation sterilization the polymerizable composition continues to maintain flowability and to be polymerization curable via UV curing.

2. The sample collection tube of claim 1, wherein the polymerizable composition is further adapted such that it can withstand irradiation sterilization at a dosage of less than 20 kGy for a period of less than two hours while maintaining the density of between 1.00-1.09 g/cm3, and, following irradiation sterilization, continues to maintain flowability and to be polymerization curable via UV curing.

3. The sample collection tube of claim 1, wherein the photoinitiator is present in a concentration of less than 2 wt % of the polymerizable composition.

4. The sample collection tube of claim 1, wherein the polymerizable composition is polymerizable by UV curing to a polymer selected from the group consisting of: an acrylate polymer, a methacrylate polymer, an epoxy polymer, a polyurethane, and a thiol-ene polymer.

5. The sample collection tube of claim 1, wherein the oligomer comprises an acrylate containing oligomer.

6. The sample collection tube of any claim 1, wherein the oligomer comprises a methacrylate containing oligomer.

7. The sample collection tube of claim 1, wherein the polymerizable composition further comprises at least one of a polymer containing a terminal epoxy group, a polymer containing a pendant epoxy group, an epoxy-siloxane resin, an epoxy-polyurethane, an epoxy-polyesters, epichlorohydrin, a polyhydric diol, and a polyhydric polyol.

8. The sample collection tube of claim 1, wherein the polymerizable composition further comprises a polymer comprising at least one of a terminal or pendant isocyanate group, a polymer comprising at least two hydroxyl groups, a polyhydric diol, and a polyhydric polyol.

9. The sample collection tube of claim 1, wherein the polymerizable composition further comprises at least one of aliphatic monomeric polythiol, an aliphatic dithiol, an aromatic dithiol, a polymeric polythiol, an acrylate, a methacrylate, an alkenyl, and a cycloalkenyl.

10. The sample collection tube of claim 1, wherein the polymerizable composition further comprises a photoinhibitor.

11. The sample collection tube of claim 1, wherein the photoinitiator is selected from the group consisting of a phosphine oxide photoinitiator, a ketone-based photoinitiator, and a benzoin ether photoinitiator.

12. The sample collection tube of claim 1, wherein the irradiation comprises at least one of gamma ray irradiation and electron beam irradiation.

13. The sample collection tube of claim 1, wherein the polymerizable composition is UV curable to a hardness of at least 10 on a Shore A hardness scale over a period of less than 60 seconds.

14. The sample collection tube of claim 1, wherein the stabilizer comprises phenothiazine.

15. The sample collection tube of claim 1, wherein tocopherol is present in the polymerizable composition at a concentration between 75 and 200 mM.

16. The sample collection tube of claim 1, wherein tocopherol is present in the polymerizable composition at a concentration between 75 and 150 mM.

17. The sample collection tube of claim 1, wherein tocopherol is present in the polymerizable composition at a concentration between 100 and 150 mM.

18. The sample collection tube of claim 1, wherein tocopherol is present in the polymerizable composition at a concentration between 100 and 250 mM.

19. The sample collection tube of claim 1, wherein tocopherol is present in the polymerizable composition at a concentration between 125 and 350 mM.

\* \* \* \* \*